(12) United States Patent
Feng et al.

(10) Patent No.: US 8,870,892 B2
(45) Date of Patent: Oct. 28, 2014

(54) DEVICE FOR PUNCTURING BODY AND INTRODUCING CATHETER

(76) Inventors: Qingliang Feng, Dongguan (CN); Yonghao Jiang, Dongguan (CN)

( * ) Notice: Subject to any disclaimer, the term of this patent is extended or adjusted under 35 U.S.C. 154(b) by 225 days.

(21) Appl. No.: 13/519,656

(22) PCT Filed: Sep. 1, 2010

(86) PCT No.: PCT/CN2010/076530
§ 371 (c)(1),
(2), (4) Date: Jun. 28, 2012

(87) PCT Pub. No.: WO2011/079620
PCT Pub. Date: Jul. 7, 2011

(65) Prior Publication Data
US 2012/0296255 A1   Nov. 22, 2012

(30) Foreign Application Priority Data

Dec. 31, 2009 (CN) .................. 2009 2 0296113 U
Aug. 11, 2010 (CN) ..................... 2010 1 0251090

(51) Int. Cl.
*A61F 11/00* (2006.01)
*A61M 29/00* (2006.01)
*A61B 17/34* (2006.01)
*A61M 25/06* (2006.01)

(52) U.S. Cl.
CPC ............ *A61M 29/00* (2013.01); *A61B 17/3415* (2013.01); *A61M 25/0612* (2013.01); *A61B 17/3496* (2013.01); *A61M 25/0668* (2013.01)
USPC .......................................................... 606/108

(58) Field of Classification Search
CPC ..................... A61M 25/0612; A61M 25/0668; A61M 29/00; A61B 17/3415; A61B 17/3496
USPC ............... 604/158, 160–161, 164.01, 164.05, 604/164.12, 164.13, 528; 606/528, 108
See application file for complete search history.

(56) References Cited

U.S. PATENT DOCUMENTS

| | | | | |
|---|---|---|---|---|
| 1,527,291 A | * | 2/1925 | Zorraquin | 604/158 |
| 4,306,562 A | * | 12/1981 | Osborne | 604/523 |
| 4,969,875 A | * | 11/1990 | Ichikawa | 604/164.1 |

* cited by examiner

*Primary Examiner* — Theodore Stigell

(57) ABSTRACT

A device for puncturing body and introducing catheter includes a puncture needle, a guide wire, a peelable catheter sheath, and a puncture protector. The peelable catheter sheath includes an outer sheath and an inner sheath inserted into the outer sheath and having an expansible performance. The inner sheath has a hollow internal cavity, and the guide wire can pass through the hollow internal cavity. The puncture protector includes an inner core, a nut and a spring. The inner core has an inner core head, an inner core tail, and an inner core lumen. The nut has a nut lumen. The inner core is surrounded by the spring, one end of which abuts against the nut, and the other end of which is fastened to the inner core. The inner core tail lies within the nut lumen. The guide wire matches with the inner core lumen.

5 Claims, 10 Drawing Sheets

60

71  73  72
  70

DEVICE FOR PUNCTURING BODY AND INTRODUCING CATHETER

FIELD OF THE INVENTION

The present invention relates to medical instrumentation, and more specifically to a device for puncturing body and introducing catheter.

BACKGROUND OF THE INVENTION

During the procedure of treating a patient, sometimes it needs to introduce a catheter into the body of the patient thereby conducting body effusion out from the body or conducting medicine or nourishment etc. into the body. Now, the commonly used surgical method is to introduce a catheter after surgery, taking example for ventriculo-peritoneal shunt, the traditional method of which needs to cut the abdominal wall to introduce the catheter in the abdominal cavity. Such method has the drawbacks of long operation time, large injury and the risk of intestinal adhesion, intestinal obstruction and abdominal hernia, at the same time, the patient needs to lie in bed, the recovery speed is slow, and the abdomen is left behind operational scars.

As the development of minimally invasive surgery theory in recently years, it has reported to introduce the peritoneal ventricle end by puncturing peritoneum and introducing catheter. Now, by reviewing literature, the mainly methods of introducing the ventricle and peritoneal shunt catheter by puncturing peritoneum are as follows: (1) Some scholars try to use the method of abdominal puncture to introduce the peritoneal shunt catheter to avoid the postoperative complications of opening surgery, however it uses the self-made puncturing needle or uses the big suction head in neurosurgery to polish into puncturing needle to puncture the peritoneum, or uses a steel tube and a kirschner wire to puncture the peritoneum; (2) it is also reported to introduce the catheter with the auxiliary of laparoscopy and pneumoperitoneum apparatus.

The self-made puncturing needle or the puncturing needle that is polished into by the big suction head in neurosurgery, or the steel tube and the kirschner wire have the drawback of large puncturing injury. Moreover they can't be bought in the market, so it is difficult for popularization and application. The method of introducing the catheter with the auxiliary of laparoscopy and pneumoperitoneum apparatus is high reliable, the drawback of which is need two teams of practitioners, one team of which drill core and dig tunnel, and the other team control the abdomen. Therefore, it is necessary to research a system for puncturing abdomen for the ventriculo-peritoneal shunt.

SUMMARY OF THE INVENTION

To overcome the above-mentioned drawbacks, an object of the present invention is to provide a device for puncturing abdomen and introducing catheter, which has the advantageous of not cutting the abdominal wall, littler injury and postoperative sequelae, simple and safety operation, minimal invasion, low operation cost and not leaving behind operational scars in the abdomen.

A device for puncturing abdomen and introducing catheter adapted for guiding a peritoneal end of a shunt catheter into an abdominal cavity during ventriculo-peritoneal shunt comprises a puncture needle with a hollow inner cavity adapted for puncturing the abdomen, and being characterized in further comprises:

a guide wire which matches with the hollow inner cavity of the puncture needle so as to run through the hollow inner cavity of the puncture needle and enter the abdominal cavity, and so that the puncture needle is pulled out along the guide wire; and a peelable catheter sheath which comprises an outer sheath and an inner sheath inserted into the outer sheath and having an expansible performance, the inner sheath has a hollow internal cavity matching with the guide wire so as to guide the peelable catheter sheath into the abdominal cavity along the guide wire, the outer sheath is kept in the abdominal cavity after taking out the guide wire and the inner sheath in turn for guiding the peritoneal end of the shunt catheter into the abdominal cavity.

The guide wire has a J-shaped end.

The outer sheath of the peelable catheter sheath is made from polytetrafluoroethylene, and the inner sheath is made from polypropylene.

The device for puncturing peritoneal and introducing catheter further includes a syringe. After the puncture needle is inserted into the abdominal cavity, the puncture needle connects with the syringe full of normal saline. Observe whether the normal saline flows into the abdominal cavity under the function of weight power or not, and detect whether the puncture needle lies in the abdominal cavity or not.

The above device for puncturing abdomen and introducing catheter avoids cutting the abdominal wall in ventriculo-peritoneal shunt, it is little in injury and postoperative sequelae, simple and safety for operation. However, after the puncture needle enters into the abdominal cavity, the practitioner can not intuitively observe the location of the puncture needle in it, which is judged by right of the practitioner's experience. This would inevitably cause some errors. Especially for the inexperienced practitioners, it possibly happens the accident that after the puncture needle enters into the abdominal cavity, it runs out again. Therefore, on the basis of the above device for puncturing abdomen and introducing catheter, the applicant of the present invention develops an improved device for puncturing body and introducing catheter which has a puncturing protector. On one hand, the puncturing protector makes the practitioner intuitively observe the location of the puncture needle in the abdominal cavity after the puncture needle enters into the abdominal cavity, thereby avoiding accident. On the other hand, the device for puncturing abdomen and introducing catheter is not only suitable for introducing the catheter into the abdominal cavity in ventriculo-peritoneal shunt, but also suitable for tubing in cystostomy, tubing in gastrostomy, shunting abdominal cavity, draining pleural effusion operations, etc.

A device for puncturing body and introducing catheter comprises:

a puncture needle which has a taper puncture needle head, a puncture needle tail, and a hollow inner cavity of the puncture needle that runs through the taper puncture needle head and the puncture needle tail;

a guide wire;

a peelable catheter sheath which comprises an outer sheath and an inner sheath inserted into the outer sheath and has an expansible performance, the inner sheath has a hollow internal cavity, the guide wire is able to pass through the hollow internal cavity of the inner sheath; and a puncture protector, which comprises:

an inner core that has an inner core head, an inner core tail, and an inner core lumen which runs through the inner core head and the inner core tail;

a nut that has a nut lumen which runs therethrough; and a spring surrounding the inner core, one end of which abuts against the nut, and the other end of which is fixed to the inner core;

the inner core head passes through the inner cavity of the puncture needle and is exposed outside of the puncture needle head, and the inner core tail lies within the nut lumen;

the guide wire matches with the inner core lumen so as to pass through the inner core lumen.

The puncture protector further comprises a protection sleeve, which has a protection sleeve lumen running therethrough, the protection sleeve lumen has a first chamber, a second chamber and a third chamber, part of the nut is fixedly contained in the first chamber, the spring is telescopically and movably contained in the second chamber, the puncture needle tail is contained in the third chamber and fixed to the third chamber.

The nut has a first and a second junctions; the nut lumen runs through the first and the second junctions; the second junction holds in the first chamber; the inner core tail locates in the nut lumen where the second junction lies, the first junction is provided with a port for connecting with a syringe.

The length of the nut lumen where the first junction lies is equal to or less than the length of the inner core head; the length of the inner core head is equal to or less than the length of the s spring when compressed.

The inner core head is provided with a notch, and the notch communicates with the inner core lumen.

The inner core is provided with an inner core plug, one end of the inner core plug is arc-shaped, the other end of the inner core plug is able to enter the inner core lumen from the inner core head, thereby sealing the inner core lumen.

The advantageous of the present invention are as follows: the device for puncturing abdomen and introducing catheter in the present invention avoids cutting the abdominal wall in ventriculo-peritoneal shunt, which has the advantageous of littler injury and postoperative sequelae, simple and safety operation, low operation cost and suitable for popularization and application. Especially on the basis of the above device for puncturing abdomen and introducing catheter, the applicant of the present invention develops an improved device for puncturing body and introducing catheter which includes a puncturing protector. The puncturing protector is helpful for observing the location of the puncture needle in the abdominal cavity, thereby avoiding the puncturing needle piercing the organ and bringing a great amount of convenience for operations.

DETAILED DESCRIPTION OF ILLUSTRATED EMBODIMENTS

Figure 1A:
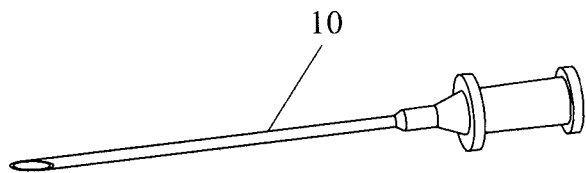
FIGS. 1a-1e respectively shows the puncture needle 10, the guide wire 20, the outer sheath 31 and the inner sheath 32 of the peelable catheter sheath, the peelable catheter sheath 30 and the syringe 40 in the device for puncturing peritoneal and introducing catheter in the present invention.
Figure 1B:
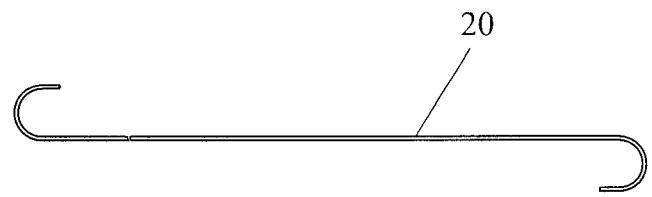
Figure 1C:
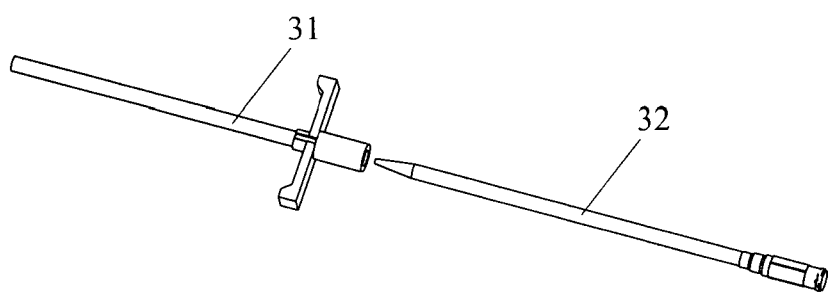
Figure 1D:
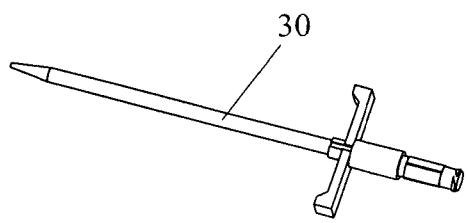
Figure 1E:
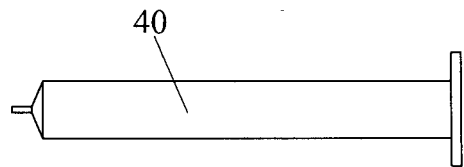
Figure 2A:
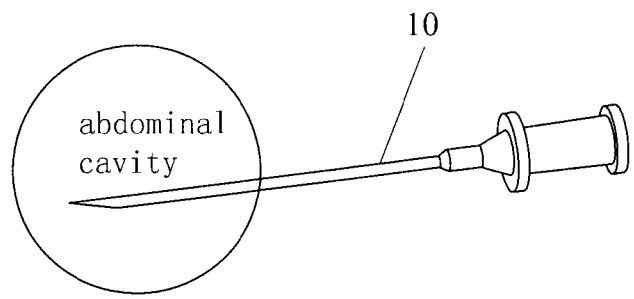
FIG. 2a-2d show the processes of that after the puncture needle 10 is inserted into the peritoneal, one end of the guide wire 20 passes through the inner cavity of the puncture needle 10 and enters the abdominal cavity, and the puncture needle 10 is pulled out along the other end of the guide wire 20, therefore one end of the guide wire 20 is left in the abdominal cavity.
Figure 2B:
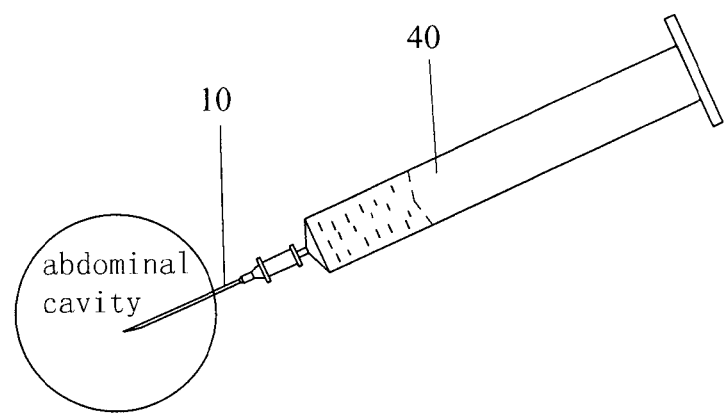
Figure 2C:
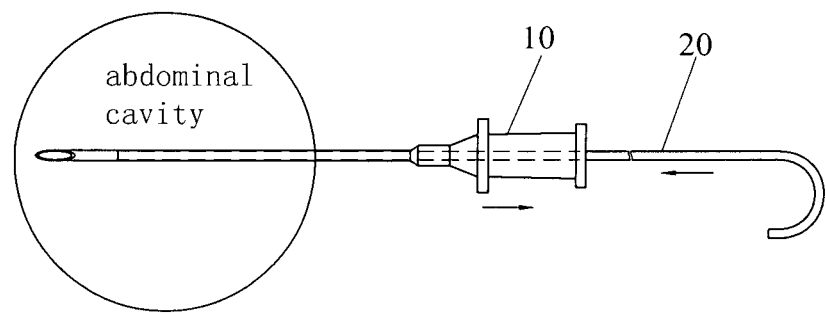
Figure 2D:
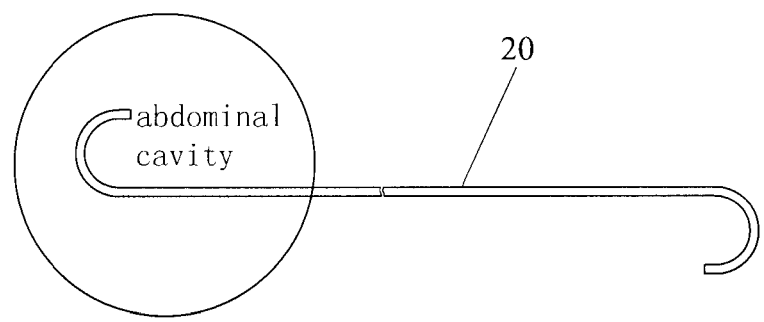
Figure 3A:
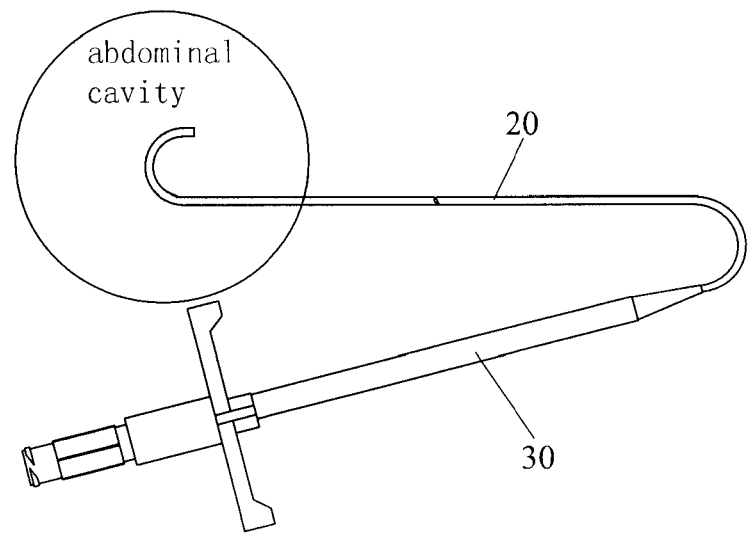
FIG. 3a-3f show the processes of that the other end of the guide wire 20 passes through the inner sheath 32 of the peelable catheter sheath 30, the peelable catheter sheath 30 is implanted into the abdominal cavity along the guide wire 20, the guide wire 20 and the inner sheath are taken out, the peritoneal end 82 of the shunt catheter is inserted into the abdominal cavity, the outer sheath 31 is peeled and the peritoneal end 82 of the shunt catheter is inserted into the abdominal cavity and left there.
Figure 3B:
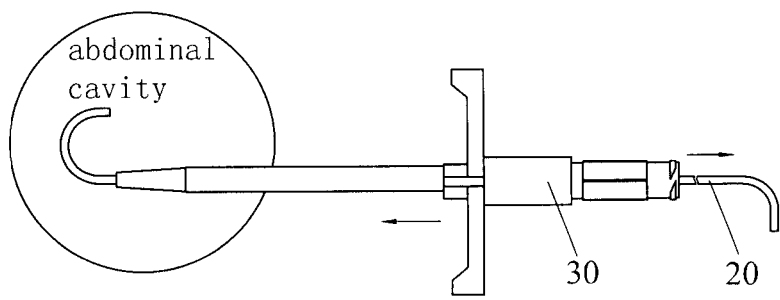
Figure 3C:
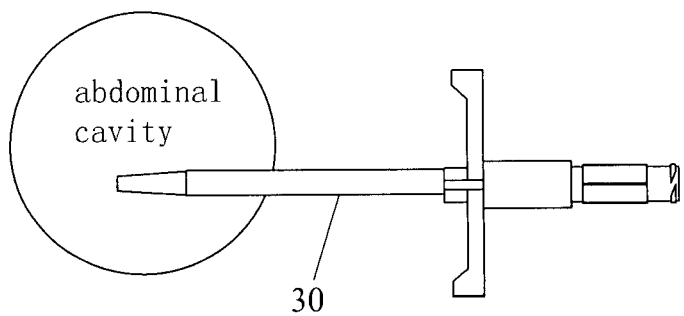
Figure 3D:
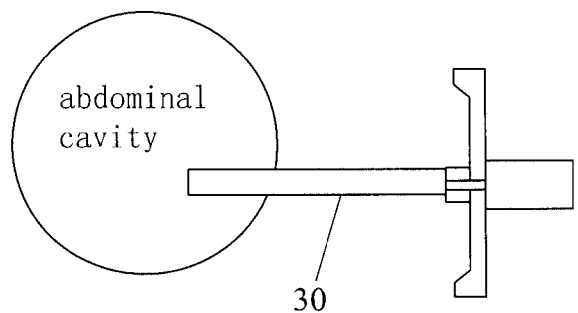
Figure 3E:
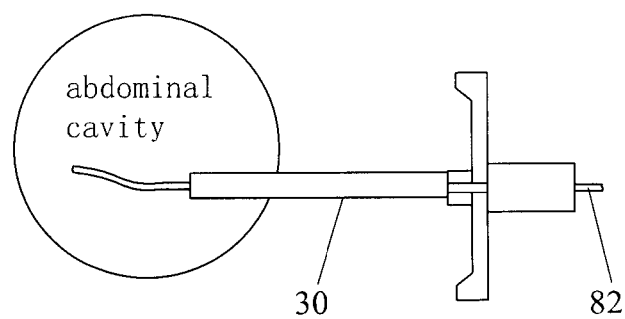
Figure 3F:
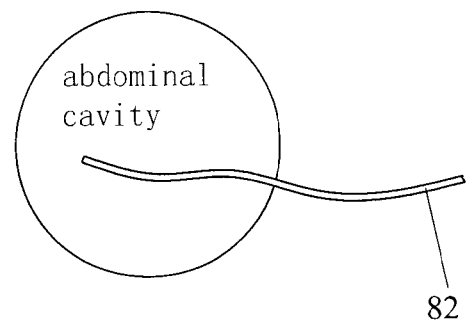

In order to concretely illustrate the device for puncturing abdomen and introducing catheter in the present invention, the follow will further illustrate with specific embodiments and the drawings.

Referring to FIG. 1a, FIG. 1b, FIG. 1c, FIG. 1d and FIG. 1e, the device for puncturing abdomen and introducing catheter, adapted for guiding a peritoneal end of a shunt catheter into an abdominal cavity in ventriculo-peritoneal shunt, comprises a puncture needle 10 with a hollow inner cavity adapted for puncturing the abdominal cavity; the guide wire 20, which has a J-shaped end and is a kind of soft wire; the peelable catheter sheath 30, which comprises an outer sheath 31 and an inner sheath 32 inserted into the outer sheath 31 and having an expansible performance, the inner sheath has a hollow internal cavity. Preferably, the device for puncturing peritoneal and introducing catheter also includes a syringe 40.

FIG. 2a, FIG. 2b, FIG. 2c and FIG. 2d show the processes of that after the puncture needle 10 is inserted into the abdominal cavity, one end of the guide wire 20 passes through the inner cavity of the puncture needle 10 and enters into the abdominal cavity, and the puncture needle 10 is pulled out along the other end of the guide wire 20, therefore one end of the guide wire 20 is left in the abdominal cavity. The guide wire 20 matches with the inner cavity of the puncture needle 10 and the internal cavity of the inner sheath 32. In ventriculo-peritoneal shunt, after the puncture needle 10 is inserted into the abdominal cavity, observing with a laparoscopy, the puncture needle 10 does not damage the abdominal viscera and the vascular, and the liquid is no drawn out from the abdominal viscera and the vascular. The puncture needle 10 connects with the syringe 40 without suppository, the normal saline is filled in the spring 40 and if the normal saline flows into the abdominal cavity under the function of weight power, it shows that the puncture needle lies in the right place. One end of the guide wire 20 passes through the inner cavity of the puncture needle 10 and enters the abdominal cavity, and the puncture needle 10 is pulled out along the other end of the guide wire 20, therefore one end of the guide wire 20 is left in the abdominal cavity.

FIG. 3a, FIG. 3b, FIG. 3c, FIG. 3d, FIG. 3e and FIG. 3f show the processes of that the other end of the guide wire 20 passes through the inner sheath 32 of the peelable catheter sheath 30, the peelable catheter sheath 30 is implanted into the abdominal cavity along the guide wire 20, the guide wire 20 and the inner sheath are taken out. The other end of the guide wire 20 passes through the inner sheath 32 of the peelable catheter sheath 30, the peelable catheter sheath 30 is implanted into the abdominal cavity along the guide wire 20, the guide wire 20 and the inner sheath are taken out in turn, the peritoneal end 82 of the shunt catheter is inserted into the abdominal cavity along the outer sheath, then the outer sheath 31 is peeled and the peritoneal end 82 of the shunt catheter is left in the abdominal cavity.

In surgery, the peritoneal end 82 of the shunt catheter communicates with the encephalocoele end of the shunt catheter, then the hydrocephalus is transferred to the abdominal cavity with the function of the pressure power.

The outer sheath 31 of the peelable catheter sheath 30 is made from polytetrafluoroethylene, and the inner sheath 32 is made from polypropylene.

Referring to FIG. 1b, FIG. 1c, FIG. 1d and FIG. 1e, the device for puncturing body and introducing catheter comprises the guide wire 20, the peelable catheter sheath 30, which includes the outer sheath 31 and the inner sheath 32, the syringe 40. Referring to FIG. 4a, FIG. 4b, FIG. 4c, FIG. 4d and FIG. 4e, the device for puncturing body and introducing catheter comprises the puncture needle 10', which has a taper puncture needle head 12, a puncture needle tail 13 and an inner cavity of the puncture needle 11 that runs through the puncture needle head 12 and the puncture needle tail 13. The device for puncturing body and introducing catheter also comprises a puncture protector 100, the puncture protector 100 comprises the inner core 50, the spring 60 and the nut 70. The inner core 50 has an inner core head 53, an inner core tail 52, an inner core lumen 51 which runs through the inner core head 53 and the inner core tail 52. The inner core head 53 is provided with a notch 56, the notch 56 communicates with the inner core lumen 51. The nut 70 has a hollow nut lumen 71 which runs through the nut.

Figure 4A:
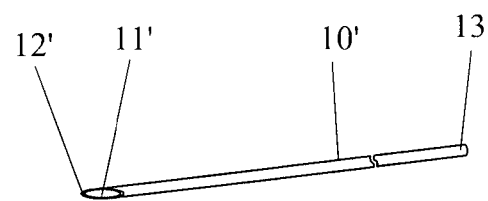
FIG. 4a-4e respectively shows the perspective view of the puncture needle 10' in the second embodiment, the second embodiment of the inner core 50, the spring 60 and the nut 70 of the puncture protector 100 in the device for puncturing peritoneal and introducing catheter in the present invention.
Figure 4B:
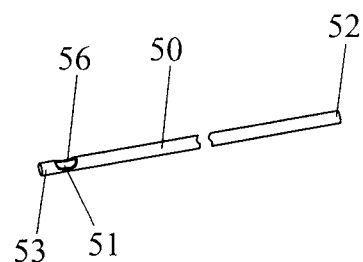
Figure 4C:
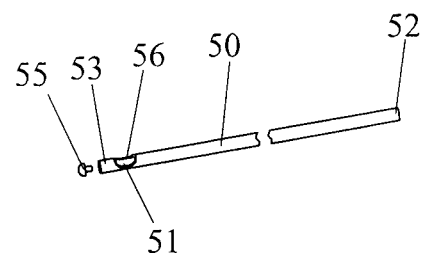
Figure 4D:
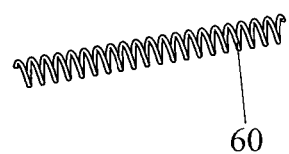
Figure 4E:
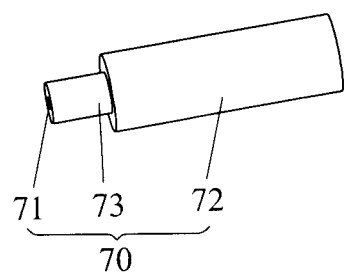

Referring to FIG. 4b, the inner core head 53 is arc-shaped.

Referring to FIG. 4b, the inner core 50 is provided with an inner core plug 55, one end of the inner core plug 55 is arc-shaped, the other end of the inner core plug passes through the inner core head 53 and enters into the inner core lumen 51, thereby sealing it.

Figure 5A:
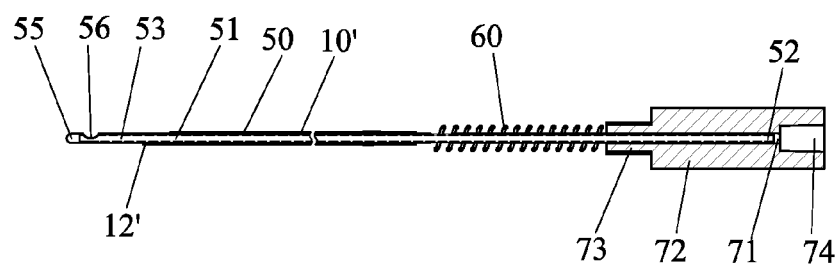
FIG. 5a shows the perspective view of the second embodiment that the puncture needle 10' and the puncture protector is used in conjunction, which includes the puncture needle 10', the joint together inner core 50, the spring 60 and the nut 70.

Referring to FIG. 5a, the inner core head 53 passes through the inner cavity 51 of the puncture needle and is exposed outside of the puncture needle head 12. The inner core tail 52 lies within the nut lumen 71. The spring 60 surrounds the inner core 50, and one end of the circle shaped spring 60 abuts against the nut 70, the other end of the spring is fixed to the inner core 50. The inner core 50 is able to displace in the inner cavity of the puncture needle 11 and the lumen 71 of the nut.

The guide wire 20 matches with the lumen of the inner core 51, and the guide wire 20 is able to enter the lumen of the inner 51 from the inner core tail 52 and runs out from the notch 56, thereby introducing the puncture needle 10 and the puncture protector 100 to lead out from the other end of the guide wire 20.

Take example for the catheterized surgery of the peritoneal end of the shunt catheter in ventriculo-peritoneal shunt, when the puncture needle 10 and the puncture protector 100 enter the abdominal cavity, the practitioner controls the nut 70, the inner core head 53 suffers resistance opposite to its advancing direction and displaces opposite to its advancing direction in the inner core 51 and the lumen of the nut 70. Because one end of the spring 60 abuts against the inner core 50, and the other end fixed connects the nut 70, while the practitioner controls the nut not to move, the spring 60 will be compressed, thereby controlling the distance that the inner core 50 displaces in the lumen of the inner core 51 and the lumen of the nut 71. As the displacement of the inner core 50, the inner core tail 52 also displaces in the lumen of the nut 71. For convenience for the practitioner to observe, the nut 70 is provided with a transparent window at the position where the inner core tail 71 lies, or the length of the lumen of the nut 7 is define 1 so as to the circle shaped spring 60 is compressed, the inner core tail 52 exerts the lumen of the nut 71. When the puncture needle 10 enters the abdominal cavity, the resistance suffered by the inner core head disappears, the circle shaped spring 60 is not compressed and recovers its original length, the inner core head 52 exerts the puncture needle head 12, and the inner core tail 72 recovers its original place. Then the practitioner can observe the displacement of the inner core tail 52 and judge the displacement of the inner core 50 thereby knowing the place of the puncture needle 10 in the abdominal cavity.

Figure 5B:
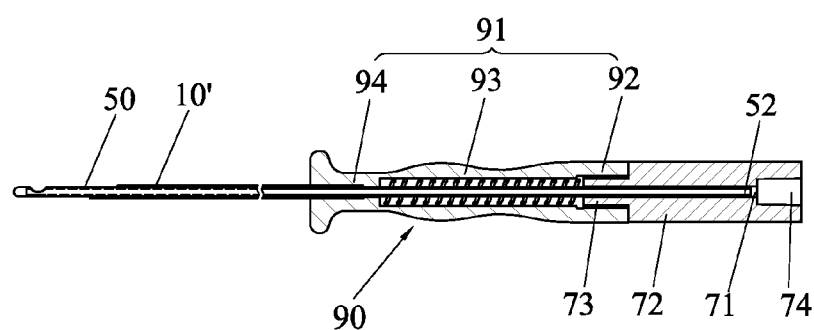
FIG. 5b shows another perspective view of the embodiment that the puncture needle 10' and the puncture protector is used in conjunction, the puncture needle 10', the inner core 50, the spring 60 and the nut 70 are used in conjunction with the protection sleeve 90.

FIG. 5b, FIG. 5b shows another example of the puncture protector. The puncture protector also has a protection sleeve 90, the protection sleeve 90 has a protection sleeve lumen 91 running through it, the protection sleeve lumen 91 has a first chamber 92, a second chamber 93 and a third chamber 94, part of the nut 70 is fixedly contained in the first chamber 92, the spring 60 is contained in the second chamber 93 and can move forward and backward in it, part of the puncture needle 10 is contained in the third chamber 94 and fixedly connects with the third chamber 94. The nut 70 has the first and the second junctions 72 and 73; the nut lumen 71 runs through the first and the second junctions 71 and 73; the second junction 73 holds in the first chamber 92; the inner core tail 52 locates in the nut lumen 71 where the second junction 73 lies.

Take example for the catheterized surgery of the peritoneal end of the shunt catheter in ventriculo-peritoneal shunt, when the puncture needle 10' and the puncture protector 100 enter the abdominal cavity, the inner core head 53 suffers resistance opposite to its advancing direction and displaces opposite to its advancing direction in the inner core 51 and the lumen of the nut 70. Because one end of the spring 60 abuts against the inner core 50, and the other end fixedly connects the nut 70, while the nut 70 is fixed by the second junction 73 in the first chamber 92 of the protect sleeve, the spring 60 will be compressed, thereby controlling the distance that the inner core 50 displaces in the lumen of the inner core 51 and the lumen of the nut 71. For convenience for the practitioner to observe the displacement of the inner core 50 in the lumen of the inner core 51 and the lumen of the nut, the length of the inner core head 53 is equal to or less than the length of the s spring 60 when compressed, the length of the nut lumen 71 where the first junction 72 lie is equal to or less than the length of the inner core head 53. When the inner core displaces, the inner core tail 52 will exert the lumen of the nut 70, which will beneficial for observing for the practitioner. Preferably, for more convenience for the practitioner to observe the displacement of the inner core tail 52, the nut 70 and the protection sleeve 90 both are made from transparent material. When the puncture needle 10' enters the abdominal cavity, the resistance suffered by the inner core head 53 disappears, the spring 60 is not compressed and recovers its original length, the inner core head 53 exerts the puncture needle head 12, the inner core tail 52 goes back to the nut lumen 71 where the second junction lies.

Preferably, the first junction 72 is provided with a port 74 along the nut lumen, the port 74 can be connected with the syringe 40. After the puncture needle is inserted into the abdominal cavity, the port 74 connects with the syringe full of normal saline. Observe whether the normal saline flows into the abdominal cavity under the function of weight power or not, and detect whether the puncture needle 10' lies in the abdominal cavity or not.

Figure 6A:
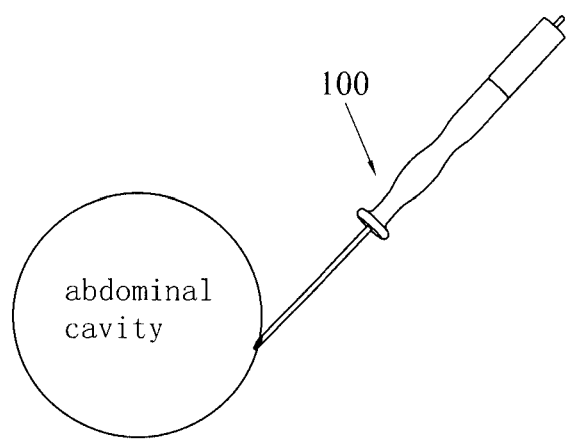
FIG. 6a-6e show the processes of that after the puncture needle 10' and the puncture protector 100 are inserted into the abdominal cavity, one end of the guide wire 20 passes through the lumen 51 of the inner core and enters the abdominal cavity, the puncture needle 10' and the puncture protector 100 are pulled out along the other end of the guide wire 20, and one end of the guide wire 20 is left in the abdominal cavity.
Figure 6B:
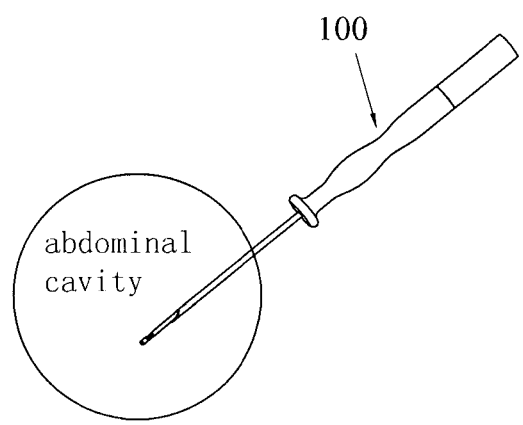
Figure 6C:
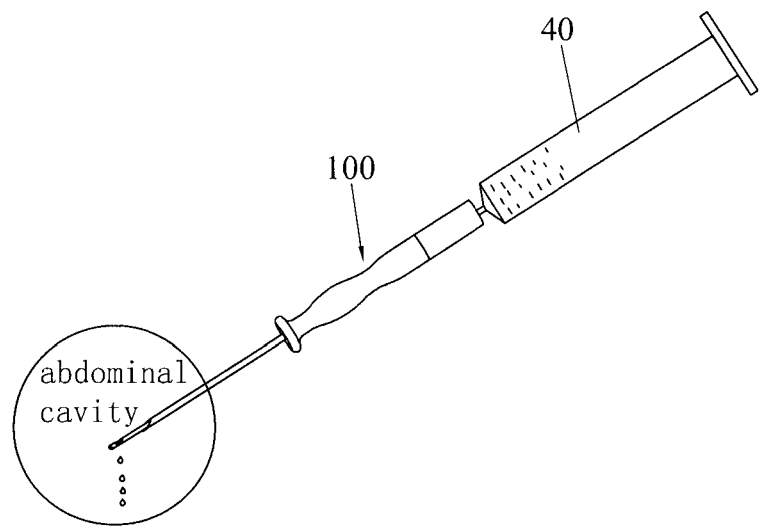

Referring to FIG. 6a, FIG. 6b, FIG. 6c, FIG. 6d and FIG. 6e, taking example for the catheterized surgery of the peritoneal end of the shunt catheter in ventriculo-peritoneal shunt, these figures show the processes that the guide wire enters the abdominal cavity by using the device for puncturing body and introducing catheter. Referring to FIG. 6a, when the puncture needle 10' of the device for puncturing body and introducing catheter, the inner core head 53 suffers resistance opposite to its advancing direction and displaces opposite to its advancing direction, the spring 60 will be compressed, thereby controlling displacement of the inner core 50. The practitioner can observe that the inner core tail 52 will displace in the nut lumen 71 and exert the nut lumen 71 along the opposite direction to its advancing direction. Referring to FIG. 6b, after the puncture needle 10' is inserted into the abdominal cavity, the resistance suffered by the inner core head 53 disappears, the spring 60 is not compressed, the inner core head 53 exerts the puncture needle head 12, the inner core tail 52 will displace in the nut lumen 71 and enter the nut lumen 71 along the same direction to its advancing direction. Referring to FIG. 6c, after the puncture needle 10' is inserted into the abdominal cavity, observing with a laparoscopy, the puncture needle 10' does not damage the abdominal viscera and the vascular, and the liquid is no drawn out from the abdominal viscera and the vascular. The puncture needle 10' connects with the syringe 40 without suppository, the normal saline is filled in the spring 40 and if the normal saline flows into the abdominal cavity under the function of weight power, it shows that the puncture needle lies in the right place.

Figure 6D:
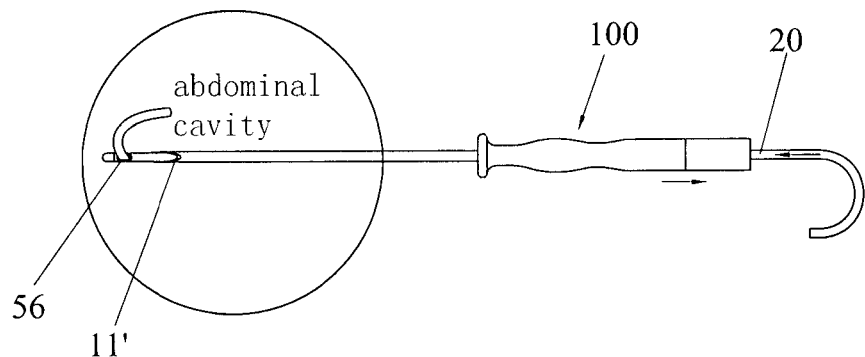
Figure 6E:
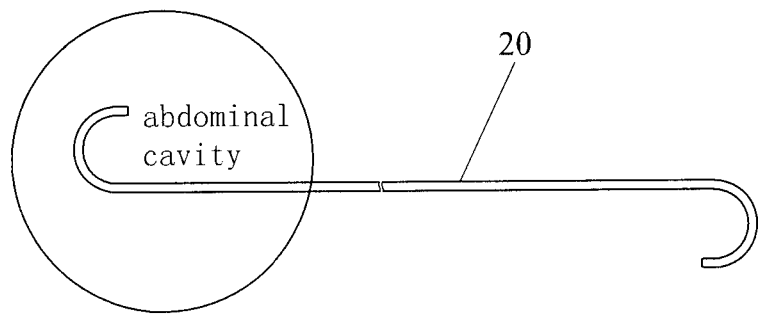

Referring to FIG. 6d and FIG. 6e, after the puncture needle 10' and the puncture protector 100 are inserted into the abdominal cavity, one end of the guide wire 20 is passed through the lumen 51 of the inner core and enters the abdominal cavity through the notch 56, after that, the puncture needle 10' and the puncture protector 100 are pulled out along the other end of the guide wire 10', and one end of the guide wire 20 is left in the abdominal cavity.

Referring to FIG. 3a, FIG. 3b, FIG. 3c, FIG. 3d, FIG. 3e and FIG. 3f, these figures show the processes of that the other end of the guide wire 20 passes through the inner sheath 32 of the peelable catheter sheath 30, the peelable catheter sheath 30 is implanted into the abdominal cavity along the guide wire 20, the guide wire 20 and the inner sheath are taken out. The lumen of the inner sheath 32 of the peelable catheter sheath 30 matches with the guide wire 20. The guide wire 20 passes through the inner sheath 32 of the peelable catheter sheath 30, the peelable catheter sheath 30 is implanted into the abdominal cavity along the guide wire 20, the guide wire 20 and the inner sheath 32 are taken out in turn, the peritoneal end 82 of the shunt catheter is inserted into the abdominal cavity along the outer sheath, then the outer sheath 31 is peeled and the peritoneal end 82 of the shunt catheter is left in the abdominal cavity.

In surgery, the peritoneal end 82 of the shunt catheter communicates with the encephalocoele end of the shunt catheter, then the hydrocephalus is transferred to the abdominal cavity with the function of the pressure power.

It is worth to noticing that the above embodiments take example for the catheterized surgery of the peritoneal end of the shunt catheter in ventriculo-peritoneal shunt, discretely illustrate the using process of the device for puncturing body and introducing catheter. However the device for puncturing body and introducing catheter in the present invention is not limited in the abdominal cavity. The other surgeries that need to introduce catheter in the body, for examples in cystostomy, tubing in gastrostomy, shunting abdominal cavity, draining pleural effusion etc. also can use the device for puncturing body and introducing catheter in the present invention.

The above embodiments are only the prefer examples of the present invention, and they are not to limit the practical range of the present invention, any obviously modifications and variations according to the structure, characteristics and principle that disclosed in the claims in the present invention are intended to be include within the scope of this invention as defined by the accompanying claims.

What is claimed is:

1. A device for puncturing body and introducing catheter, comprising:
    a puncture needle, said puncture needle having a taper puncture needle head, a puncture needle tail, and a hollow inner cavity that runs through said taper puncture needle head and said puncture needle tail;
    a guide wire;
    a peelable catheter sheath, said peelable catheter sheath comprising an outer sheath and an inner sheath inserted into the outer sheath and having an expansible performance, said inner sheath having a hollow internal cavity, said guide wire being able to pass through said hollow internal cavity of said inner sheath; and
    a puncture protector which comprises:
    an inner core, said inner core having an inner core head, an inner core tail, and an inner core lumen which runs through said inner core head and said inner core tail;
    a nut, said nut having a nut lumen which runs therethrough; and
    a spring, said inner core being surrounded by the spring, one end of the spring abutting against said nut, and the other end of the spring being fixed to said inner core;
    wherein said inner core head passes through said hollow inner cavity of the puncture needle and is exposed outside of said puncture needle head, and said inner core tail lies within said nut lumen;
    wherein said guide wire matches with said inner core lumen so as to pass through said inner core lumen;
    wherein said puncture protector further comprising a protection sleeve which has a protection sleeve lumen running there through, said protection sleeve lumen has a first chamber, a second chamber, and a third chamber, part of said nut is fixedly contained in said first chamber, said spring is telescopically and movably contained in said second chamber, said puncture needle tail is contained in said third chamber and fixed to said third chamber;
    wherein said inner core contains in said puncture needle, said protection sleeve and said nut.

2. The device for puncturing body and introducing catheter according to claim 1, wherein said nut has a first and a second junctions, said nut lumen runs through said first and said second junctions, said second junction holds in said first chamber, said inner core tail locates in the nut lumen where the second junction lies, and said first junction is provided with a port for connecting with a syringe.

3. The device for puncturing body and introducing catheter according to claim 2, wherein the length of the nut lumen where said first junction lies is equal to or less than the length of said inner core head, and the length of said inner core head is equal to or less than the length of the spring when compressed.

4. The device for puncturing body and introducing catheter according to claim 1, wherein said inner core head is provided with a notch, and said notch communicates with said inner core lumen.

5. The device for puncturing body and introducing catheter according to claim 1, wherein said inner core is provided with an inner core plug, one end of said inner core plug is arc-shaped, and the other end of said inner core plug is able to enter said inner core lumen from said inner core head, thereby sealing said inner core lumen.

\* \* \* \* \*